United States Patent [19]

Smith et al.

[11] Patent Number: 4,945,095
[45] Date of Patent: Jul. 31, 1990

[54] METHOD FOR SUPPRESSING THE IMMUNE RESPONSE

[76] Inventors: Sidney R. Smith, 700 Spring Ave., Ridgewood, N.J. 07450; Marvin I. Siegel, 507 Maple Hill Dr., Woodbridge, N.J. 07095

[21] Appl. No.: 808,404

[22] Filed: Dec. 12, 1985

[51] Int. Cl.$^5$ .............................................. A61K 31/44
[52] U.S. Cl. .................................... 514/278; 514/885
[58] Field of Search ........................ 514/278, 825, 885

[56] References Cited

U.S. PATENT DOCUMENTS

| | | | |
|---|---|---|---|
| 4,378,365 | 3/1983 | Durant et al. | 514/825 X |
| 4,499,100 | 2/1985 | Kluge et al. | 514/321 |
| 4,632,923 | 12/1986 | Blythin | 514/247 |
| 4,652,564 | 3/1987 | Blythin | 514/248 |

OTHER PUBLICATIONS

Wolff, "Berger's Medicinal Chemistry", Fourth Edition, Part III, pp. 554–555, 1253–1255 (1981).

*Primary Examiner*—Leonard Schenkman
*Attorney, Agent, or Firm*—Gerald S. Rosen; James R. Nelson

[57] ABSTRACT

A method and composition for suppressing the immune response are disclosed which employ an immunosuppressing effective amount of certain substituted spiro pyridine derivatives.

15 Claims, No Drawings

METHOD FOR SUPPRESSING THE IMMUNE RESPONSE

BACKGROUND OF THE INVENTION

The present invention relates to the use of certain substituted spiro pyridine derivatives in suppressing the immune response.

The preparation of a spiro[cyclopentane]-quinolinedione is described in Chem. Pharm. Bull., 17, 1290 (1969). Several additional spiroquinoline diones are disclosed in Bull. Soc. Chim. Fr., 364 (1968). The references do not describe pharmaceutical uses for these compounds.

SUMMARY OF THE INVENTION

The present invention is drawn to a method for suppressing the immune response in a mammal which comprises administering to a mammal in need of such treatment an immunosuppressing effective amount of a compound having the structural formula I:

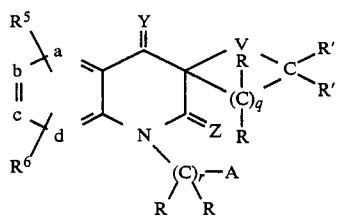

or solvate thereof, wherein:

two of the ring groups a,b,c and d may be CH or N and the remaining two groups represent CH;

Y and Z independently represent O or S;

V represents O, $S(O)_n$,

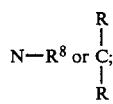

each R independently represents hydrogen, $C_1$ to $C_6$ alkyl, $CH_2OH$, $COR_7$ (wherein $R^7$ represents hydrogen or $C_1$ to $C_6$ alkyl) or hydroxy, with the proviso that only one hydroxy group can be attached to one carbon atom;

each R' independently is as defined for R above, except that when V represents O, $S(O)_n$ or $N-R^8$, R' may not be hydroxy;

$R^8$ is hydrogen, alkyl having from 1 to 6 carbon atoms, carboxylic acyl having from 2 to 7 carbon atoms, alkylsulfonyl having from 1 to 6 carbon atoms, carboalkoxy having from 2 to 7 carbon atoms, $CONH_2$, phenyl or pyridyl of which the last two may be substituted with up to three substituents, Q, whereby each Q independently is hydroxy, alkyl having from 1 to 6 carbon atoms, halogen, nitro, alkoxy having from 1 to 6 carbon atoms, trifluoromethyl, cyano, cycloalkyl having from 3 to 7 carbon atoms, alkenyloxy having from 3 to 6 carbon atoms, alkynyloxy having from 3 to 6 carbon atoms, $S(O)_n$-$R^a$ {wherein n is defined herein and $R^a$ is alkyl having from 1 to 6 carbon atoms}, $NHSO_2R^a$ {wherein $R^a$ is defined herein}, $NHSO_2CF_3$, $SO_2NH_2$, $COR^b$ {wherein $R^b$ is OH, $NH_2$ or $OR^a$ (wherein $R^a$ is defined herein)}, O-B-$COR^b$ {wherein B is alkylene having from 1 to 4 carbon atoms and $R^b$ is defined herein}, or $NHCOR^c$ {wherein $R^c$ is hydrogen, alkyl having from 1 to 6 carbon atoms, alkoxy having from 1 to 6 carbon atoms, $COR^d$ (wherein $R^d$ is hydroxy or alkoxy having from 1 to 6 carbon atoms) or $NHR^e$ (wherein $R^e$ is hydrogen or alkyl having 1 to 6 carbon atoms)};

$R^5$ and $R^6$ may be the same or different and are hydrogen, alkyl having from 1 to 6 carbon atoms, halogen, nitro, alkoxy having from 1 to 6 carbon atoms, trifluoromethyl, alkylthio having 1 to 6 carbon atoms or cyano;

n is 0, 1 or 2;

r is 0, 1 or 2;

q is an integer of from 1 to 5; and

A is phenyl, naphthyl, indenyl, indanyl, 2-, 3- or 4-pyridyl, 2-, 4-, 5- or 6-pyrimidyl, 2- or 3-pyrazinyl, 2- or 3-furyl, 2- or 3-thienyl, 2-, 4- or 5-imidazolyl, 2-, 4- or 5-thiazolyl or 2-, 4- or 5-oxazolyl, any of which may be substituted with up to three substituents Q as defined herein above.

A preferred subgenus of compounds is that wherein Y and Z are both oxygen.

Preferably, a, b and c represent CH and d is either CH or N. A further preferred feature is that r is zero, i.e. the group A is directly attached to the ring-nitrogen atom. q is preferably 2, 3 or 4, V most preferably is $CH_2$ or O and $R^5$ and $R^6$ are both hydrogen.

Particularly preferred are compounds of the structural formula II

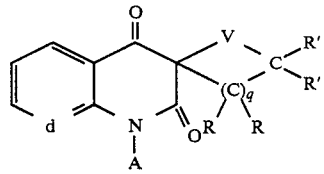

wherein d is CH or N, q is 2, 3 or 4 and A, V, R and R' are as defined above.

As disclosed in European published application No. 84114974.3 (European patent publication No. 0 144 966 A2), these compounds possess anti-allergy and anti-inflammatory activities. It has now unexpectedly been found that these compounds possess immunosuppressive activity.

DESCRIPTION OF THE INVENTION

When utilized herein and in the appended claims the below listed terms, unless specified otherwise, are defined as follows:

halogen - comprises fluorine, chlorine, bromine and iodine;

alkyl and alkoxy - comprises straight and branched carbon chains containing from 1 to 6 carbon atoms;

alkenyloxy - comprises straight and branched carbon chains containing from 3 to 6 carbon atoms and comprising a carbon to carbon double bond; and alkynyloxy - comprises straight and branched carbon chains containing from 3 to 6 carbon atoms and comprising a carbon to carbon triple bond.

The compounds of the invention include a

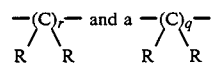

substituent wherein the R groups may vary independently. Thus, for example, when r or q equals 2 the following patterns of substitution (wherein hydrogen and $CH_3$ are used to represent any substituents R) are contemplated: —C(CH₃)₂CH₂—, —CH₂C(CH₃)₂—, —CH₂CH(CH₃)—, —CH(CH₃)CH₂—, —(C(CH₃)H)₂— and the like. In addition when r or q equals 2, substituents such as —C(CH₃)₂CH(C₂H₅)—, —CH(CH₃)CH(C₂H₅) are also contempleted.

It would be obvious to one of ordinary skill in the art that due to problems of stability there are limitations involving the R and R' groups. One limitation is that neither R can be a hydroxy group attached to the carbon alpha to the ring nitrogen atom. Another limitation is that the R and R' groups cannot both be hydroxy groups attached to the same carbon atoms.

Certain compounds of the invention may exist in isomeric forms. The invention contemplates all such isomers both in pure form and in admixture, including racemic mixtures. In the structural formulas I and II herein, when V represents a hetero atom in the spiro ring, V is attached directly to the spiro carbon atom, i.e., the carbon atom identified as number 3 in structural formula I.

The compounds of formula I can exist in unsolvated as well as solvated forms, including hydrated forms. In general, the solvated forms, with pharmaceutically acceptable solvents such as water, ethanol and the like are equivalent to the unsolvated forms for purposes of the invention.

Representative compounds of formula I are exemplified below in Table I:

disclosures of which are incorporated herein by reference for that purpose.

The compounds are useful in the treatment of autoimmune and other immunological diseases including graft rejection in which T cell proliferation is a contributing factor to the pathogenesis of disease. The effectiveness of these compounds as immunosuppressing agents may be demonstrated by the following tests which involve the inhibition of T cell functions using these compounds.

GRAFT VS. HOST REACTION (GVHR)

To induce a GVHR, C57 B1/6XA/J(B6AF1) male mice were injected intravenously with parental (C57B1/6J) spleen and lymph node cells. The compound 1-phenyl-3',4',5',6'-tetrahydro-spiro-[1,8]-naphthyridine-3,2'[2H]pyran]-2,4-dione ¼ hydrate (Compound A) was then administered orally for 10 days beginning on the day prior to the cell transfer. On the day following the last treatment, the animals were sacrificed, and their spleens were excised and weighed. The enlargement of the spleen of the host is a result of a GVHR. To some extent it is the host's own cells which infiltrate and enlarge the spleen although they do this because of the presence of graft cells reacting against the host. The amount of spleen enlargement, splenomegaly, is taken as a measure of the severity of the GVHR.

TABLE I

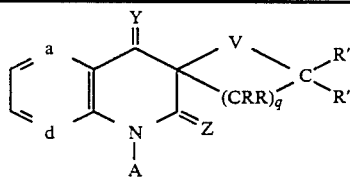

| Compound No. | d | a | A | Y | Z | V | —CR'R'—(CRR)q— | m.p. (°C.) |
|---|---|---|---|---|---|---|---|---|
| 1 | N | CH | phenyl | O | O | CH₂ | trimethylene | 174–178 |
| 2 | N | CH | 3-hydroxyphenyl | O | O | CH₂ | trimethylene | 218–220 |
| 3 | N | CH | 3-methoxyphenyl | O | O | CH₂ | trimethylene | 159–160.5 |
| 4 | CH | CH | phenyl | O | O | CH₂ | trimethylene | 168–168 |
| 5 | N | CH | 3,4-chlorophenyl | O | O | CH₂ | trimethylene | 143–145.5 |
| 6 | N | CH | 4-chlorophenyl | O | O | CH₂ | trimethylene | 168.5–172 |
| 7 | N | CH | 4-methylphenyl | O | O | CH₂ | trimethylene | 177–178.5 |
| 8 | N | CH | 3-chlorophenyl | O | O | CH₂ | trimethylene | 165–167 |
| 9 | N | CH | 3-chlorophenyl | S | O | CH₂ | trimethylene | 168–170 |
| 10 | N | CH | phenyl | S | O | CH₂ | trimethylene | 188–189.5 |
| 11 | N | CH | 3-ethyloxalylamino phenyl | O | O | CH₂ | trimethylene | 158–160 |
| 12 | N | CH | 3-fomylaminophenyl | O | O | CH₂ | trimethylene | 222–224 |
| 13 | N | CH | 3-aminophenyl | O | O | CH₂ | trimethylene | 200–202 |
| 14 | N | CH | 3-(ethyloxycarbonylmethoxy)phenyl | O | O | CH₂ | trimethylene | 103–105 |
| 15 | N | CH | phenyl | O | O | O | trimethylene | 241.5–243 (¼ hydrate) |
| 16 | N | CH | phenyl | O | O | O | ethylene | 233–235.5 |
| 18 | N | CH | phenyl | O | O | S | trimethylene | |
| 19 | N | CH | 3,4-dichlorophenyl | O | O | O | tetramethylene | |
| 20 | N | CH | 3-chlorophenyl | O | O | O | tetramethylene | 158.5–160 |
| 21 | N | CH | 4-chlorophenyl | O | O | O | tetramethylene | 229–231.5 (hemihydrate) |
| 22 | N | CH | 3-methoxyphenyl | O | O | O | tetramethylene | 181–183 |
| 23 | N | CH | 4-methoxyphenyl | O | O | O | tetramethylene | |

The compounds which are utilized in the method of this invention are among those disclosed in U.S. application Ser. No. 561,416 filed Dec. 14, 1983, in U.S. application Ser. No. 641,076, filed Aug. 15, 1984, and in European Published Patent Application No. 841149743 (publication number: 0 144 966 A2). These compounds may be prepared by methods described in those U.S. applications and European published application, the In carrying out the GVHR the animal in the experimental group is injected with parental cells, cells of the same species but of different genotype, which cause a weight increase of the spleen. The animal in the control group is injected with syngeneic cells, genetically identical cells which do not cause a weight increase of the spleen. The effectiveness of Compound A administered to the mice in the experimental group is measured by comparing the spleen weight of the untreated and treated GVH animal with that of the syngeneic control. Compound A reduced spleen weight by 30% as compared to the untreated animals at a dose of 100 mg/kg, i.e., $ED_{30}=100$ mg/kg.

SPLENIC ATROPHY

The immunosuppressive activity of the compounds may also be shown by a decrease in spleen weight after dosing $BDF_1$ mice orally with the drug for seven (7) consecutive days. The mice are sacrificed on the eighth day. The percent decrease in spleen weight is measured for each dosage level. In this procedure 1'-(3-chlorophenyl)-spiro-[cyclopentane-1,3'-[1,8 ]-naphthyridine]-2'-4'-(1'H)-dione (Compound B) provided a 30% spleen weight decrease at a dosage level of 100 mg/kg.

As noted, European patent publication No. 0 144 966 A2 discloses that the subject compounds possess anti-allergy and anti-inflammatory activities. For example, Compound A has an $ED_{50}$ value of about 2 mg/kg p.o. in tests measuring the inhibition of anaphylactic bronchospasm in sensitized guinea pigs having antigen-induced bronchoconstriction and an $ED_{50}$ value of about 19 mg/kg p.o. in tests measuring the reverse passive Arthus reaction in the pleural cavity of rats (as described by Myers et al., *Inflammation*, Vol. 9 , No. 1 , 1985, pp. 91– 98). Compound A has an $ED_{30}$ value of about 100 mg/kg in the GVHR test as described above. These results for Compound A and similar results obtained for other compounds of formula I tested to date indicate that an immunosuppressive effective dose ($ED_{30}$) for such compounds is about 5 times or more their anti-inflammatory and anti-allergy effective doses ($ED_{50}$s).

The usual dosage range for the compounds of formula I in a 70 kg mammal is an oral dose of about 0.1 to 250 mg/kg, preferably 0.1 to 150 mg/kg, in 3 or 4 divided doses per day. Of course, the dose will be regulated according to the potency of compound employed, the immunological disease being treated, and the judgment of the attending clinician depending on factors such as the degree and the severity of the disease state and age and general condition of the patient being treated.

To treat immunological diseases, the active compounds of formula I can be administered in unit dosage forms such as tablets, capsules, pills, powders, granules, sterile parenteral solutions or suspensions, suppositories, transdermal compositions and the like. Such dosage forms are prepared according to standard techniques well known in the art.

For preparing pharmaceutical compositions from the compounds described by this invention, inert, pharmaceutically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to about 70 percent of the active ingredient. Suitable solid carriers are magnesium carbonate, magnesium strearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution or suspension in aqueous polyethylene glycol solution. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in additions to the active material, flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

The composition of the invention may also be deliverable transdermally. The transdermal compositions can take the form of creams, lotions and/or emulsions and can be included in a transdermal patch of the matrix or reservoir type as are conventional in the art for this purpose.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be appropriate number of any of these in packaged form. The compositions can, if desired, also contain other therapeutic agents.

The dosages may be varied depending upon the requirements of the patient, the severity of the condition being treated and the particular compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following examples are intended to illustrate, but not to limit, the present invention. The term "Compound A" refers to 1'-phenyl-3',4',5',6'-tetrahydrospiro-[1,8]naphthyridine -3',2'-[2H]-pyran]-2,4-dione ¼ hydrate. It is contemplated, however, that this compound may be replaced by equally effective quantities of other compounds of formula I as defined above.

EXAMPLE 1

| No. | Ingredient | m/tablet | mg/tablet |
|---|---|---|---|
|  | Tablets |  |  |
| 1 | Compound A | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Strearate | 3 | 7 |
|  | Total | 300 | 700 |

Method of Manufacture

Mix Item Nos. 1 and 2 in a suitable mixture for 10–15 minutes. Granulate the mixture with Item No. 3. Mill the damp granules through a coarse screen (e.g., ¼") if needed. Dry the damp granules. Screen the dried granules if needed and mix with the Items No. 4 and mix for 10–15 minutes. Add Item No. 5 and mix for 1–3 minutes. Compress the mixture to appropriate the size and weight on a suitable tablet machine.

EXAMPLE 2

| No. | Ingredient | mg/capsule | mg/capsule |
|---|---|---|---|
|  | Capsules |  |  |
| 1. | Compound A | 100 | 500 |
| 2. | Lactose USP | 106 | 123 |
| 3. | Corn Starch, Food Grade | 40 | 70 |
| 4. | Magnesium Strearate NF | 4 | 7 |
|  | Total | 250 | 700 |

Method of Manufacture

Mix Item Nos. 1,2 and 3 in a suitable blender for 10–15 minutes. Add Item No. 4 and mix for 1–3 minutes. Fill the mixture into suitable two-piece hard gelatin capsules on a suitable encapsulating machine.

EXAMPLE 3

| Parenteral |  |  |
|---|---|---|
| Ingredient | mg/vial | m/vial |
| Compound A Sterile Powder | 100 | 500 |

Add sterile water for injection or bacteriostatic water for injection for reconstruction.

EXAMPLE 4

| No. | Ingredient | mg/vial | mg/vial |
|---|---|---|---|
|  | Injectable |  |  |
| 1. | Compound A | 100 | 500 |
| 2. | Methylparaben | 1.8 | 1.8 |
| 3. | Propylparaben | 0.2 | 0.2 |
| 4. | Sodium Bisulfite | 3.2 | 3.2 |
| 5. | Disodium Edetate | 0.1 | 0.1 |
| 6. | Sodium Sulfate | 2.6 | 2.6 |
| 7. | Water for Injection q.s. ad | 1.0 ml | 1.0 ml |

Method for Manufacture

1. Dissolve parabens in a portion (85% of the final volume) of the water for injection at 65°–70° C.
2. Cool to 25°–35° C. Charge and dissolve the sodium bisulfite, disodium edetate and sodium sulfate.
3. Charge and dissolve drug.
4. Bring the solution to final volume by added water for injection.
5. Filter the solution through 0.22 membrane and fill into appropriate containers.
6. Terminally sterilize the units by autoclaving.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A method for suppressing T cell functions of the immune response in a mammal which comprises administering to a mammal in need of such treatment an immunosuppressing effective amount of a compound having the structural formula I:

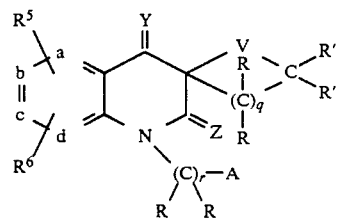

or solvate thereof, wherein:
two of the ring groups a, b, c and d may be CH or N and the remaining two groups represent CH;
Y and Z independently represent O or S;
V represents O, $S(O)_n$,

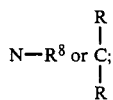

each R independently represents hydrogen, $C_1$ to $C_6$ alkyl, $CH_2OH$, $COR_7$ (wherein $R^7$ represents hydrogen or $C_1$ to $C_6$ alkyl) or hydroxy, with the proviso that only one hydroxy group can be attached to one carbon atom;

each R' independently is as defined for R above, except that when V represents O, $S(O)_n$ or $N-R^8$, R' may not be hydroxy;

$R^8$ is hydrogen, alkyl having from 1 to 6 carbon atoms, carboxylic acyl having from 2 to 7 carbon atoms, alkylsulfonyl having from 1 to 6 carbon atoms, carboalkoxy having from 2 to 7 carbon atoms, $CONH_2$, phenyl or pyridyl of which the last two may be substituted with up to three substituents, Q, whereby each Q independently is hydroxy, alkyl having from 1 to 6 carbon atoms, halogen, nitro, alkoxy having from 1 to 6 carbon atoms, trifluoromethyl, cyano, cycloalkyl having from 3 to 7 carbon atoms, alkenyloxy having from 3 to 6 carbon atoms, alkynyloxy having from 3 to 6 carbon atoms, $S(O)_n-R^a$ {wherein n is defined herein and $R^a$ is alkyl having from 1 to 6 carbon atoms}, $NHSO_2R^a$ {wherein $R^a$ is defined herein}, $NHSO_2CF_3$, $SO_2NH_2$, $COR^b$ {wherein $R^b$ is OH, $NH_2$ or $OR^a$ (wherein $R^a$ is defined herein)}, $O-B-COR^b$ {wherein B is alkylene having from 1 to 4 carbon atoms and $R^b$ is defined herein}, or $NHCOR^c$ {wherein $R^c$ is hydrogen, alkyl having from 1 to 6 carbon atoms, alkoxy having from 1 to 6 carbon atoms, $COR^d$ (wherein $R^d$ is hydroxy or alkoxy having from 1 to 6 carbon atoms) or $NHR^e$ (wherein $R^e$ is hydrogen or alkyl having 1 to 6 carbon atoms)};

$R^5$ and $R^6$ may be the same or different and are hydrogen, alkyl having from 1 to 6 carbon atoms, halogen, nitro, alkoxy having from 1 to 6 carbon atoms, trifluoromethyl, alkylthio having 1 to 6 carbon atoms or cyano;

n is 0, 1 or 2;

r is 0, 1 or 2;

q is an integer of from 1 to 5; and

A is phenyl, naphthyl, indenyl, indanyl, 2-, 3- or 4-pyridyl, 2-, 4-, 5- or 6-pyrimidyl, 2- or 3-pyrazinyl, 2- or 3-furyl, 2- or 3-thienyl, 2-, 4- or 5-imidazolyl, 2-, 4- or 5-thiazolyl or 2-, 4- or 5-oxazolyl, any of which may be substituted with up to three substituents Q as defined herein above.

2. A method according to claim 1 wherein Y and Z in formula I are both oxygen.

3. A method according to claim 2 wherein r in formula I is zero.

4. A method according to claim 3 wherein $R^5$ and $R^6$ in formula I are both hydrogen.

5. A method according to claim 4 wherein all of a, b, c, and d in formula I are CH.

6. A method according to claim 4 wherein a and d in formula I are both N and b and c are both CH.

7. A method according to claim 4 wherein d in formula I is N and a, b and c are CH.

8. A method according to claim 7 wherein q in formula I is 2, 3 or 4.

9. A method according to claim 8 wherein R and R' in formula I independently are hydrogen, methyl, ethyl, propyl, isopropyl, n-butyl or iso-butyl.

10. A method according to claim 9 wherein A in formula I is phenyl or phenyl substituted with one or two substituents Q.

11. A method according to claim 10 wherein V in formula I is O, $S(O)_n$ or $N-R^8$.

12. A method according to claim 11 wherein V in formula I is O.

13. A method according to claim 1 wherein the compound administered comprises:
1'-phenyl-spiro[cyclopentane-1,3'-(1-8)naphthyridine]-2',4'-(1'H)-dione;
1'-phenyl-spiro[cyclopentane-1,3'-quinoline]-2',4'-(1'H)-dione;
1'-(4-methylphenyl)spiro[cyclopentane-1,3'-(1,8)naphthyridine]-2',4'-(1'H)-dione;
1'-(4-chlorophenyl)spiro[cyclopentane-1,3'-(1,8)naphthyridine]-2',4'-('H)-dione;
1'-(3,4-dichlorophenyl)spiro[cyclopentane-1,3'-(1,8)naphthyridine]-2',4'-(1'H)-dione;
1'-(3-chlorophenyl)spiro[cyclopentane-1,3'-(1,8)naphthyridine]-2',4'-(1'H)-dione;
1'-(3-methoxyphenyl)spiro[cyclopentane-1,3'-(1,8)naphthyridine]-2',4'-(1'H)-dione;
1'-(3-hydroxyphenyl)spiro[cyclopentane-1,3'-(1,8)naphthyridine]-2',4'-(1'H)-dione;
1'-phenylspiro[cyclopentane-1,3'-quinoline]-2',4'-(1'H)-dione;
1-phenyl-3',4',5',6'-tetrahydrospiro[1,8-naphthyridine-3,2'-(2H)pyran]-2,4-dione;
1-(3-methoxyphenyl)-3',4',5',6'-tetrahydrospiro[1,8-naphthyridine-3,2'-(2H)pyran]-2,4-dione;
4,5-dihydro-1'-phenyl-spiro[furan-2(3H),3'(2'H)(1,8)naphthyridine]-2',4'(1'H)-dione;
1-phenyl-spiro[1,8-naphthyridine-3,2'-oxetane]-2,4-dione;
1-(3-chlorphenyl)-3',4',5',6'-tetrahydrospiro[1,8-naphthyridine-3,2'-(2H--)pyran]-2,4-dione; or a solvate thereof.

14. The method according to claim 1 wherein the compound is administered orally.

15. The method according to claim 13 wherein the compound is administered orally.

* * * * *

UNITED STATES PATENT AND TRADEMARK OFFICE
CERTIFICATE OF CORRECTION

PATENT NO. : 4,945,095

DATED : July 31, 1990

INVENTOR(S) : Sidney R. Smith and Marvin I. Siegel

It is certified that error appears in the above—identified patent and that said Letters Patent is hereby corrected as shown below:

ON TITLE PAGE:

[73] Assignee: Schering Corporation, Kenilworth, New Jersey

Signed and Sealed this

Nineteenth Day of November, 1991

Attest:

HARRY F. MANBECK, JR.

*Attesting Officer*　　　　　　　　*Commissioner of Patents and Trademarks*